(12) United States Patent
Ludescher et al.

(10) Patent No.: US 7,592,447 B2
(45) Date of Patent: Sep. 22, 2009

(54) PROCESS FOR PRODUCTION OF INTERMEDIATES FOR USE IN CEFALOSPORIN SYNTHESIS

(75) Inventors: Johannes Ludescher, Breitenbach (AT); Hubert Sturm, Innsbruck (AT); Katja Vorndran, Kufstein (AT)

(73) Assignee: Sandoz AG, Basel (CH)

( * ) Notice: Subject to any disclaimer, the term of this patent is extended or adjusted under 35 U.S.C. 154(b) by 522 days.

(21) Appl. No.: 10/583,159

(22) PCT Filed: Dec. 22, 2004

(86) PCT No.: PCT/EP2004/014646

§ 371 (c)(1),
(2), (4) Date: Jun. 16, 2006

(87) PCT Pub. No.: WO2005/063772

PCT Pub. Date: Jul. 14, 2005

(65) Prior Publication Data

US 2007/0191601 A1  Aug. 16, 2007

(30) Foreign Application Priority Data

Dec. 23, 2003 (AT) ................ A 2076/2003

(51) Int. Cl.
*C07D 501/48* (2006.01)
*C07D 501/56* (2006.01)
(52) U.S. Cl. ........................ 540/215; 540/222
(58) Field of Classification Search ............ 540/222, 540/215
See application file for complete search history.

(56) References Cited

U.S. PATENT DOCUMENTS

| 4,406,899 A | | 9/1983 | Aburaki et al. |
|---|---|---|---|
| 4,474,779 A | | 10/1984 | Nagano et al. |
| 5,594,131 A | * | 1/1997 | Lim et al. .................. 540/222 |
| 2007/0111980 A1 | * | 5/2007 | Parthasaradhi Reddy et al. . 514/202 |

FOREIGN PATENT DOCUMENTS

| DE | 3626375 A1 | 2/1987 |
|---|---|---|
| EP | 0612752 A1 | 8/1994 |
| GB | 2165245 A1 | 4/1986 |

OTHER PUBLICATIONS

Yong Sup Lee et, al.: "Synthesis and structure-activity relationships of quaternary ammonium cephalosporins with hydroxylated alicyclic or aliphatic amines" Journal of Antibiotics, vol. 47, No. 5, 1994, pp. 609-612, XP008047135 p. 609-610.
Donald G. Walker et,al: Use of bistrimethylsilylated intermediates in the preparation of semisynthetic 7-amino-3-substituted-cephems.

Journal of Organic Chemistry, vol. 53, No. 5, 1988, pp. 983-991, XP002328374, US American Chemical Society, Easton, pp. 984-985.

* cited by examiner

*Primary Examiner*—Mark L Berch
(74) *Attorney, Agent, or Firm*—Jeffrey S. Melcher; Manelli Denison & Selter PLLC

(57) ABSTRACT

A process for the production of intermediates having a formula IA

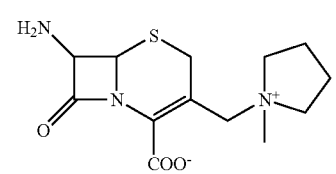

that can be used for the synthesis of cephalosporins, such as cefepime of formula V. The intermediates of formula IA are produced by desilyation of a compound of formula II

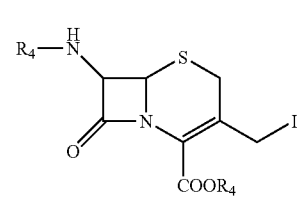

wherein R4 is a silyl-protecting group, with a protic solvent to obtain a compound of formula III,

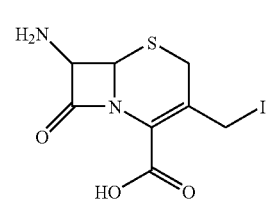

and reacting the compound of formula III with an organic base of formula IV

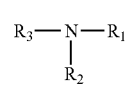

wherein R2 and R3 together represent a C4-alkylene group, and with the adjacent nitrogen atom form a saturated 5-membered heterocycle, and R1 represents a methyl group, to obtain the compound of formula 1A.

30 Claims, No Drawings

PROCESS FOR PRODUCTION OF INTERMEDIATES FOR USE IN CEFALOSPORIN SYNTHESIS

The present invention relates to a process for the production of a compound of formula

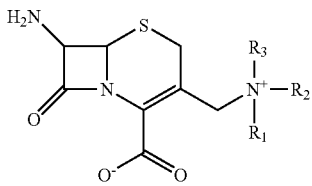

I wherein $R_1$, $R_2$ and $R_3$, independently of one another, are alkyl, alkenyl, aryl, hydroxy($C_{1-6}$)alkyl, carbamoyl-($C_{1-6}$)alkyl, amino-($C_{1-6}$)alkyl, acylamino-($C_{1-6}$)alkyl or carboxy-($C_{1-6}$)alkyl, or wherein $R_2$ and $R_3$ together with the adjacent nitrogen atom, form an alicyclic 5- to 8-membered, preferably a 5- to 6-membered, most preferably a 5-membered, alicyclic, heterocyclic ring, which, in addition to the nitrogen atom, may also contain a further 1 or 2 hetero atoms selected from the group consisting of oxygen and sulphur, preferably oxygen, and $R_1$ signifies alkyl, alkenyl or aryl, as well as a process for the production of acid addition salts and/or hydrates of a compound of formula I, comprising the reaction steps
a) desilylation of a compound of formula

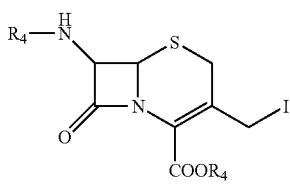

II wherein $R_4$ is a silyl-protecting group, by adding a protic solvent, in order to obtain a compound of formula

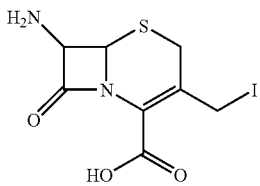

III b) reaction of the compound of formula III obtained in step a) with an organic base of formula

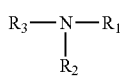

IV wherein $R_1$, $R_2$ and $R_3$ have the significances indicated above, in order to obtain a compound of formula I.

If not specified elsewhere, each organic group in the scope of this invention contains 1 to 20 carbon atoms. Alkyl is in particular ($C_{1-6}$)alkyl, preferably ($C_{1-6}$)alkyl, e.g. ($C_{1-4}$)alkyl. Alkenyl is in particular ($C_{2-8}$)alkenyl, preferably ($C_{2-4}$)alkenyl, e.g. vinyl. Aryl is in particular ($C_{6-18}$)aryl, whereby aryl may denote one ring, such as phenyl, or several rings, e.g. two anellated rings, such as naphthyl. Aryl is preferably phenyl. Acylaminoalkyl is in particular ($C_{1-12}$)-acylaminoalkyl, e.g. ($C_{1-6}$)-acylaminoalkyl.

$R_1$, $R_2$ and $R_3$, independently of one another, are alkyl, alkenyl, aryl or hydroxy($C_{1-6}$)-alkyl, especially alkyl and aryl, such as alkyl.

If $R_2$ and $R_3$, together with the adjacent nitrogen atom, form an alicyclic 5- to 8-membered heterocycle, and $R_1$ is alkyl, alkenyl or aryl, the heterocycle may be saturated or partly unsaturated. For example, a 5-membered heterocycle may contain one double bond, a 6-membered heterocycle may contain one or two double bonds, and a 7- or 8-membered heterocycle may contain 1 to 3 double bonds. There will not be any cumulative double bonds. The heterocycles may be unsubstituted or substituted, e.g. substituted once or many times, such as twice or three times, by alkyl. $R_1$ is preferably alkyl, such as methyl or ethyl, e.g. methyl. Examples of alicyclic heterocycles of formula IV are 1-methyl-pyrrolidine, 1-methyl-2,5-dihydro-1H-pyrrole, 1-methyl-piperidine, N-methyl-morpholine.

Silyl-protecting groups include the appropriate silyl-protecting groups that are known from the prior art for carboxyl and amino groups, especially trialkylsilyl, triarylsilyl, diaryalkylsilyl or aryldialkylsilyl groups, for example tert.-butyidimethylsilyl, trimethylsilyl, tri-isopropylsilyl, diphenylmethylsilyl, triethylsilyl, triphenylsilyl groups. Trialkylsilyl groups are preferred, especially trimethylsilyl groups.

A protic solvent is a proton-containing solvent, which is in a position to react with the silyl-protecting groups, in order to desilylate the protected carboxyl and amino groups, i.e. to deprotect them.

Suitable protic solvents are, in particular, alcohols, for example ($C_{1-6}$)-alcohols such as ($C_{1-4}$)-alcohols. The alcohols may be primary, secondary or tertiary alcohols. The water content of the alcohols should be below 5% by weight, preferably below 1% by weight, especially below 0.5% by weight, e.g. below 0.1% by weight, such as essentially water-free. Suitable alcohols are, for example, methanol, ethanol, isopropanol, n-propanol, glycol, 2-methyl-propan-2-ol, glycerol, propanediols or butanediols. Examples of propanediols are 1,2-propanediol or 1,3-propanediol. Examples of butanediols are 1,2-butanediol, 1,3-butanediol or 1,4-butanediol. Preferred protic solvents are 1,2-butanediol or isopropanol. A protic solvent may also be a mixture of different alcohols.

The amount of added protic solvent is not critical and may vary within a wide range. However, the amount of added protic solvent should be at least sufficient for complete desilylation of the compound of formula II, such as at least a 2-times molar excess over the compound of formula II.

A N,O-bis-silylated 3-iodomethyl-3-cephem compound of formula II may be produced in the manner known from the prior art, e.g. as described in EP612752A2 by reacting 7-amino-cephalosporanic acid (7-ACA) with a silylation agent and then reacting it with an iodizing agent.

Reaction steps a) and b) are preferably carried out in short succession, so as to suppress undesired secondary reactions such as homo-polymerisation reactions of the compound of formula III. A short succession may be achieved if e.g. the protic solvent and subsequently a compound of formula IV are added over the course of 1 hour to a solution or suspension of the compound of formula II, e.g. within 30 minutes or within 10 minutes. A further preferred embodiment consists in carrying out reaction steps a) and b) simultaneously in one reaction container. This may take place by the simultaneous or almost simultaneous addition, e.g. within 1 minute, of the protic solvent and the compound of formula IV to a solution or suspension of a compound of formula II. In this way, a compound of formula I may precipitate directly, e.g. in the form of an acid addition salt, such as in the form of the hydriodide.

The temperatures at which reaction steps a) and b) are carried out are not critical. Reaction steps a) and b) are advantageously effected at temperatures of −80° C. to +40° C., preferably −40° C. to 0° C., e.g. at −30° C. to −20° C. At higher temperatures, undesired by-products such as decomposition products of compounds of formula III are increasingly observed, and at lower temperatures the yields increase, but the reaction speeds become considerably slower.

The required amounts of compound of formula IV depend on the concentration of hydrogen ions and on the presence of further compounds, with which the compounds of formula IV can react, e.g. excess iodizing agent such as trimethyliodosilane in the solution or suspension of the compound of formula III. It is preferable to add an excess of compound of formula IV over the compound of formula III, e.g. a 1.5-times to 10-times molar excess over the compound of formula III, e.g. a 2-times to 5-times excess.

A compound of formula I may be isolated and purified by known methods, e.g. analogously to known processes. If the compound according to formula I precipitates as an acid addition salt, it can be isolated from the reaction mixture directly. To do this, the known processes may be used, e.g. purifying the precipitated compound of formula I in an aqueous or aqueous/organic phase such as dichloromethane/water using an anion exchanger. The anion exchanger used may be a commercial anion exchanger, e.g. Amberlite® LA-2. A further possibility of purifying and isolating a compound of formula I from the reaction mixture of the reaction according to the invention is an aqueous acidic extraction carried out in known manner, e.g. with dilute organic or inorganic acids, such as dilute sulphuric acid, hydrochloric acid, hydriodic acid, hydrobromic acid, trifluoroacetic acid or acetic acid, whereby the compound of formula I is precipitated from the aqueous phase e.g. by adding a counter-solvent such as acetone or isopropanol.

A compound of formula I may be obtained in free form, i.e. in the form of a betaine, in the form of an acid addition salt and/or in the form of a hydrate. Conversion of one form of the compound of formula I into another form may take place according to, e.g. analogously to known processes. In particular, acid addition salts may be obtained or converted by adding the corresponding inorganic or organic acids to a solution of the compound of formula I and subsequently precipitating. This process may be influenced by suitable conditions, e.g. adjustment of the pH value, forming a specific acid addition salt, e.g. a mono-acid addition salt or a di-acid addition salt. Preferred acid addition salts of the compound of formula I are hydrogen sulphates, hydriodides, hydrochlorides or hydrobromides. Hydriodides or hydrochlorides are preferred in particular, especially hydrochlorides, such as the monohydrochloride or dihydrochloride of a compound of formula I. Acid addition salts of compounds of formula I may also be present as hydrates, e.g. as monohydrates, dihydrates or trihydrates, e.g. monohydrates.

Hydrates of compounds of formula I may be produced in known manner, e.g. by precipitating in the presence of water.

In a particularly preferred embodiment, in a process according to the invention, a compound of formula I is obtained in the form of a monohydrochloride monohydrate.

One particularly preferred embodiment of the process according to the invention relates to the production of a compound of formula I, in which $R_2$ and $R_3$ together represent a $C_4$-alkylene group, and with the adjacent nitrogen atom, form a saturated 5-membered hetero-cycle, and $R_1$ represents a methyl group, so that a compound of formula

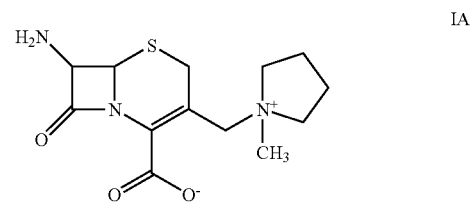

IA is obtained. As already mentioned above, a compound of formula IA can be produced as a free compound, i.e. in the betaine form, or in the form of acid addition salts and/or hydrates. Especially preferred are hydriodides such as the monohydriodide, hydrobromides such as the monohydrobromide or hydrochlorides such as the mono- or dihydrochloride, particularly in the form of a hydrate, e.g. a compound of formula IA in the form of the monohydrochloride monohydrate or in the form of a dihydrochloride monohydrate.

Compounds of formula I in free form or in the form of acid addition salts and/or in the form of hydrates are useful intermediates in the preparation of antibacterially active cephalosporins. For example, a compound of formula IA is a useful intermediate compound in the preparation of cefepime of formula V

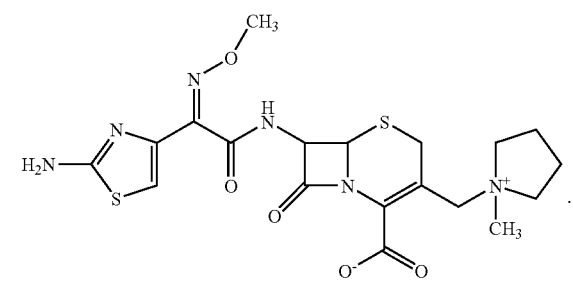

V

Therefore, in a further aspect, the present invention relates to a process for the production of cefepime of formula V or one of its acid addition salts and/or hydrates, comprising the reaction steps:

a) desilylation of a compound of formula

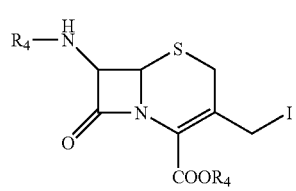

II wherein R₄ is a silyl-protecting group, by adding a protic solvent, in order to obtain a compound of formula

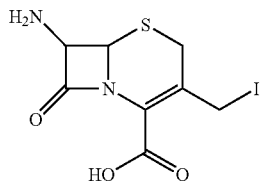

III b) reaction of the compound of formula III obtained in step a) with a strong organic base of formula

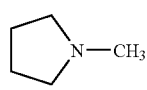

IVA in order to obtain a compound of formula

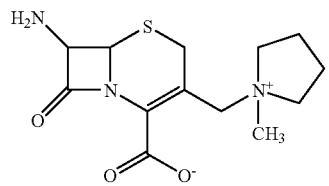

IA c) optional conversion of a compound of formula IA, as obtained from step b), into the form of an acid addition salt and/or a hydrate, and d) acylation of the 7-amino group of a compound of formula IA obtained from step b) or of its acid addition salt and/or hydrate obtained from step c), in order to obtain cefepime of formula V.

Acylation of the 7-amino group of a compound of formula IA in step d) may be carried out according to, e.g. analogously to known processes. Cefepime of formula V includes cefepime in all its forms, as are known from the prior art, e.g. from German Offenlegungsschrift DE3626375A. In particular, cefepime may exist in free form, in the form of salts, especially acid addition salts and/or in the form of solvates, e.g. hydrates.

One problem with previous processes for the production of compounds of formula I was that substantial amounts of corresponding Δ2-compounds were formed as by-products (e.g. as described by Walker et al, in J. Org. Chem. 53, 1988, p. 983 to 991, see Table 1 on page 985). Δ2-compounds have a double bond in position 2 instead of the double bond in position 3 of the cephalosporin frame. Since most of the obtainable antibiotically active cephalosporins, including cefepime, are Δ3-compounds, the Δ2-compounds have to be separated from the corresponding desired Δ3-compounds either at the stage of the intermediates of formula I or at the stage of the end products. In view of the chemical-physical similarity between the corresponding Δ3- and Δ2-compounds, separation of the Δ2-compounds is difficult and expensive. In addition, the total yield from the production process is considerably reduced, since the Δ2-compounds have to be discarded and e.g. are not available for a further reaction to form the desired Δ3 end products.

It has now surprisingly been found that, by using a process from the present invention, it is possible to virtually suppress the formation of Δ2-compounds of formula I. The Δ3/Δ2 ratio of a compound of formula I produced by a process according to the invention is greater than 95/5, e.g. greater than 99/1, in particular greater than 99.5/0.5, such as greater than 99.9/0.1. In this way, the Δ2-product of a compound of formula I produced by a process according to the invention may be present in an amount below the practicable detection limit. In addition, a process according to the invention can lead to good total yields of a Δ3-compound of formula I of e.g. more than 50%, such as more than 60% or more than 70% of the theoretical yield, based on the 7-aminocephalosporanic acid (7-ACA) employed. Evaluation of the Δ3/Δ2-ratio is effected by known analytical methods, e.g. by HLPC.

A further advantage of a process of the present invention is the saving of expensive and complex process steps for separating the undesired Δ2-compounds from the reaction mixture, as described e.g. in GB2165245A.

The good results of a process according to the invention were particularly surprising, because it would have been expected that the desilylation of the compound of formula II carried out before the nucleophilic substitution taking place on the 3-iodomethyl group would lead to increased formation of undesired by-products, e.g. homo-polymerisation compounds, owing to the particular reactivity of the 3-iodomethyl group and the unprotected 7-amino and 4-carboxyl groups of a compound of formula III. This is not the case, however, in a process according to the invention.

The following examples serve to illustrate the process according to the invention, but in no way limit the scope of the invention. All temperatures are indicated in ° celsius.

EXAMPLES

Example 1

7-amino-3-[(1-methyl-1-pyrrolidinium)methyl]ceph-3-em-4-carboxylate hydrochloride hydrate (=1-[(7-amino-2-carboxy-8-oxo-5-thia-1-azabicyclo[4.2.0]oct-2-en-3-yl)methyl]-1-methyl-pyrrolidinium-chloride hydrate or "NMP-ACA.HCl.H2O")

A solution of 76.5 g of 3-acetoxy-7-trimethylsilylamino-3-cephem-4-carboxylic acid trimethylsilylester (bissilylated 7-ACA) in 950 ml of dichloromethane is mixed at −1° C. with 40.2 ml of trimethyliodosilane (TMSI). After stirring for 17 h at −3° C., the reaction solution is cooled to −20° C. and stirred into a mixture of 200 ml of dichloromethane, 80 ml of 1,2-butanediol and 69 ml of N-methylpyrrolidine (NMPI) at −18 to −20° C. The resulting suspension is stirred for a further 15 mins at −20° C. and is subsequently added to a solution of 200 ml of water and 110 ml of conc. hydrochloric acid. After stirring vigorously for 5 mins, phase separation takes place. The aqueous phase is filled with water to 600 g. Then, 1200 ml of acetone are added, the solution is mixed with seed crystals and cooled to 0° C. The solution is left to crystallise for 1 h, then the pH value is adjusted to pH 2.5 with triethylamine, and stirred for 10 mins at room temperature (25° C.).

The precipitate is filtered off by suction and washed twice with a mixture of acetone/water (9:1) and then twice with acetone, and subsequently dried at 45° C./10 mbar over P₂O₅. 46.6 g (73% of theoretical yield) of white, crystalline NMP-ACA are obtained as the hydrochloride-monohydrate with a content of 85.6% 7-amino-3-[(1-methyl-1-pyrrolidinium) methyl]ceph-3-em-4-carboxylate. The content of 7-amino-3-

[(1-methyl-1-pyrrolidinium)methyl]ceph-2-em-4-carboxylate was less than 0.1% by weight.

NMR Data:

$^1$H-NMR (300 MHz, D$_2$O): δ (ppm)=2.14 (m, 4H, —N$^+$CH$_2$CH$_2$—); 2.93 (s, 3H, CHN$^+$—); 3.41-3.60 (m, 5H, —N$^+$CH$_2$CH$_2$—, SCH$_2$); 3.87 (d, 1H, J=16.9 Hz, SCH$_2$); 3.92, 4.67 (2b, 2H, J=13.9 Hz, —CH$_2$—N$^+$—); 4.78 (d, 1H, J=5.2 Hz, H-7); 5.13 (b, J=5.2 Hz, H-6).

M.p.: 165° C. (decomposition).

Example 2

7-amino-3-[(1-methyl-1-pyrrolidinium)methyl]ceph-3-em-4-carboxylate (NMP-ACA)

A solution of 153 g of 3-acetoxy-7-trimethylsilylamino-3-cephem-4-carboxylic acid trimethylsilylester (bissilylated 7-ACA) in 1900 ml of dichloromethane is mixed at −3° C. with 80.4 ml of trimethyliodosilane. After stirring for 17 h at −3° C., the reaction solution is cooled to −30° C. and stirred into a mixture of 2500 ml of isopropanol and 250 ml of N-methylpyrrolidine at max. 18° C. The resulting suspension is stirred for 3.5 h at 18° C. The precipitate is then filtered off by suction, washed with 1000 ml of isopropanol and 1000 ml of methylbutylether and subsequently dried in a vacuum at room temperature. 97.5 g of 7-amino-3-[(1-methyl-1-pyrrolidinium)methyl]ceph-3-em-4-carboxylate are obtained.

Example 3

7-amino-3-[(1-methyl-1-pyrrolidinium)methyl]ceph-3-em-4-carboxylic acid chloride hydrochloride hydrate (=1-[(7-amino-2-carboxy-8-oxo-5-thia-1-azabicyclo[4.2.0]oct-2-en-3-yl)methyl]-1-methyl-pyrrolidinium-chloride hydrochloride hydrate or "NMP-ACA.2HCl.H2O")

A solution of 76.5 g of 3-acetoxy-7-trimethylsilylamino-3-cephem-4-carboxylic acid trimethylsilylester (bissilylated 7-ACA) in 950 ml of dichloromethane is mixed at −1° C. with 40.2 ml of trimethyliodosilane (TMSI). After stirring for 17 h at −3° C., the reaction solution is cooled to −20° C. and stirred into a mixture of 200 ml of dichloromethane, 80 ml of 1,2-butanediol and 69 ml of N-methylpyrrolidine (NMPI) at −18 to −20° C. The resulting suspension is stirred for a further 15 mins at −20° C. and is subsequently added to a solution of 80 ml of water and 120 ml of conc. hydrochloric acid. After stirring vigorously for 5 mins, phase separation takes place.

200 ml of acetone are added dropwise to the aqueous phase in such a way that the temperature rises to a maximum of 17° C. The pH is adjusted to below pH 0.5 by adding conc. hydrochloric acid. Acetone is subsequently added until the solution becomes cloudy, and it is seeded with seed crystals. After stirring for 40 mins at 17° C., the suspension is cooled to 0° C. and stirred for 60 mins. After slowly adding a further 900 ml of acetone, the suspension is stirred at 0° C. for a further 20 mins. The crystalline precipitate is then filtered off by suction and washed twice with a mixture of acetone/water (9:1) and then twice more with acetone, and subsequently dried at 45° C./10 mbar over P$_2$O$_5$. 54.12 g (65.1% of theoretical yield) of 7-amino-3-[(1-methyl-1-pyrrolidinium)methyl]ceph-3-em-4-carboxylic acid chloride hydrochloride hydrate (NMP-ACA.2HCl.H2O) are obtained in the form of a light yellow crystalline powder.

What we claim is:

1. A process for the production of a compound of formula IA

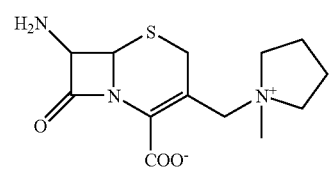

comprising the steps of:
a) desilylation of a compound of formula II,

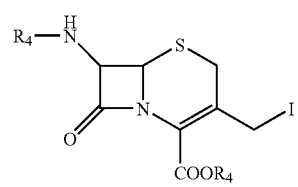

wherein R4 is a silyl-protecting group, by adding a protic solvent to obtain a compound of formula III;

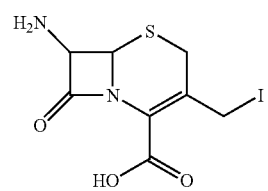

and
b) reacting the compound of formula III with an organic base of formula IV,

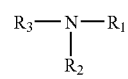

wherein R2 and R3 together represent a C4-alkylene group, and with the adjacent nitrogen atom form a saturated 5-membered heterocycle, and R1 represents a methyl group, to obtain the compound of formula 1A.

2. The process according to claim 1, wherein the protic solvent and the organic base of formula IV are added simultaneously in a reaction container.

3. The process according to claim 1, wherein the protic solvent comprises a (C$_{1-4}$)-alcohol.

4. The process according to claim 2, wherein the protic solvent comprises a (C$_{1-4}$)-alcohol.

5. The process according to claim 3, wherein the alcohol comprises methanol.

6. The process according to claim 3, wherein the alcohol comprises isopropanol.

7. The process according to 1, wherein the compound of formula IA obtained from step b) is obtained in the form of an acid addition salt and/or hydrate.

8. The process according to 1, further comprising converting the compound of formula IA obtained from step b) to the form of an acid addition salt and/or a hydrate.

9. The process according to claim 8, wherein the acid addition salt is a hydriodide or a hydrochloride.

10. The process according to claim 8, wherein the hydrate is a monohydrate.

11. The process according to claim 1, wherein the organic base of formula IV is added within 1 hour after the protic solvent is added to the compound of formula II.

12. The process according to claim 1, wherein the organic base of formula IV is added within 30 minutes after the protic solvent is added to the compound of formula II.

13. The process according to claim 1, wherein the organic base of formula IV is added within 10 minutes after the protic solvent is added to the compound of formula II.

14. The process according to claim 1, wherein the organic base of formula IV is added within 1 minute after the protic solvent is added to the compound of formula II.

15. The process according to claim 1, wherein the compound of formula 1A produced has a Δ3/Δ2 ratio of greater than 95/5.

16. The process according to claim 1, wherein the compound of formula 1A produced has a Δ3/Δ2 ratio of greater than 95/1.

17. The process according to claim 1, wherein the compound of formula 1A produced has a Δ3/Δ2 ratio of greater than 95/0.5.

18. The process according to claim 1, wherein the compound of formula 1A produced has a Δ3/Δ2 ratio of greater than 95/0.1.

19. A process for the production of cefepime of formula V

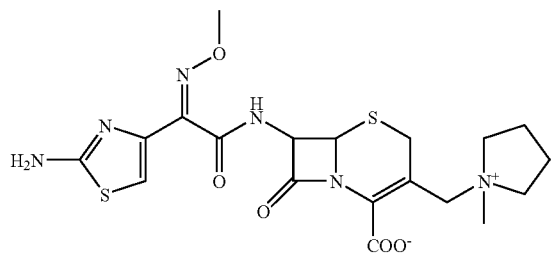

or one of its acid addition salts or its hydrates, the process comprising the steps of:

a) desilylation of a compound of formula II,

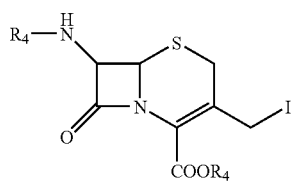

wherein R4 is a silyl-protecting group, by adding a protic solvent to obtain a compound of formula III

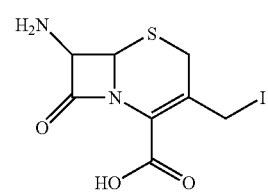

b) reacting the compound of formula III obtained in step a) with a strong organic base of formula IVA

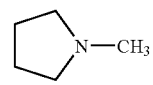

to obtain a compound of formula IA;

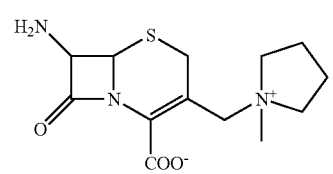

c) optional conversion of the compound of formula IA obtained from step b) into a form of an acid addition salt and/or a hydrate; and d) acylation of the 7-amino group of the compound of formula IA obtained from step b) or of its acid addition salt and/or hydrate obtained from step c) to obtain the cefepime of formula V, wherein the protic solvent and the organic base of formula IV are added simultaneously in a reaction chamber.

20. The process according to claim 1, wherein the protic solvent comprises a mixture of several ($C_{1-4}$)-alcohols.

21. The process according to claim 2, wherein the protic solvent comprises a mixture of several ($C_{1-4}$)-alcohols.

22. The process according to claim 3, wherein the alcohol comprises ethanol.

23. The process according to claim 3, wherein the alcohol comprises isopropanol.

24. The process according to claim 3, wherein the alcohol comprises n-propanol.

25. The process according to claim 3, wherein the alcohol comprises 2-methyl-propan-2-ol.

26. The process according to claim 3, wherein the alcohol comprises glycol.

27. The process according to claim 3, wherein the alcohol comprises glycerol.

28. The process according to claim 3, wherein the alcohol comprises propanediol.

29. The process according to claim 3, wherein the alcohol comprises butanediol.

30. The process according to claim 3, wherein the alcohol comprises 1,2-butanediol.

* * * * *